United States Patent [19]

Hidaka et al.

[11] 4,069,254
[45] Jan. 17, 1978

[54] ω-(ARYLSULFONAMIDO)-ALKYLAMINE

[75] Inventors: Hiroyoshi Hidaka, Kasugai; Ikuo Matsumoto, Tokyo; Masaaki Hosoi, Kawasaki; Nobuo Aoki, Utsunomiya, all of Japan

[73] Assignees: Banyu Pharmaceutical Co., Ltd., Tokyo; Hiroyoshi Hidaka, Aichi; Nobuo Aoki, Tochigi, all of Japan

[21] Appl. No.: 620,274

[22] Filed: Oct. 7, 1975

[30] Foreign Application Priority Data

Aug. 22, 1975 Japan ................ 50-101125

[51] Int. Cl.² ............... C07C 143/78; A61K 31/18
[52] U.S. Cl. .................. 260/556 AR; 260/326 R; 260/326 S; 260/349; 424/321
[58] Field of Search ................ 260/556 AR

[56] References Cited

U.S. PATENT DOCUMENTS

| 3,382,260 | 5/1968 | Gruenman et al. ...... 260/556 AR X |
| 3,580,949 | 5/1971 | Gruenman et al. ...... 260/566 AR X |
| 3,687,870 | 8/1972 | Muzyczko et al. ...... 260/556 AR X |
| 3,711,408 | 1/1973 | Karll et al. ............. 260/556 AR X |

OTHER PUBLICATIONS

Morrison & Boyd, Organic Chemistry, 3rd ed., p. 889, (1973).
The Merck Index, 7th ed., p. 1417, (1960).
Lorend et al., Biochemistry, 7, 1214, 1217, 1222, (1968).
Zucker, CA 78:69618k, (1973).
Kuranova, et al., CA 76:113506g, (1972).
Kirsanov et al., CA 58:3341e, (1963).
Shoeb et al., CA 64:9710g, (1966).
Stenberg et al., CA 76:41826m, (1972).
Stenberg et al., J. Med. Chem., 1972, vol. 15, No. 6, pp. 674–675.

Primary Examiner—Daniel E. Wyman
Assistant Examiner—Thomas A. Waltz
Attorney, Agent, or Firm—Oblon, Fisher, Spivak, McClelland & Maier

[57] ABSTRACT

ω-(Arylsulfonamido)-alkylamines having the formula $$R'\text{-}SO_2NH(CH_2)_nR \qquad \text{I}$$

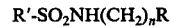

wherein R represents an amino group which can be acylated; R' represents phenyl or naphthyl which can be substituted by halogen or lower alkyl; and n represents an integer from 5 – 8 are effective in inhibiting blood platelet aggregation.

9 Claims, No Drawings

ω-(ARYLSULFONAMIDO)-ALKYLAMINE

DETAILED DESCRIPTION OF THE PREFERRED EMBODIMENTS

The present invention relates to a process for producing ω-(arylsulfonamido)-alkylamines having the formula $$R'-SO_2NH(CH_2)_nR \qquad \text{I}$$

wherein R represents an amino group which can be acylated; R' represents phenyl or naphthyl which can be substituted by halogen or lower alkyl; and $n$ represents an integer from 5 – 8. In the process of the invention, a compound having formula (I) can be produced by reacting an aliphatic diamine having the formula $$R\text{-}(CH_2)_nNH_2 \qquad \text{II}$$

wherein R and $n$ are defined above, with an arylsulfonyl halide having the formula $$R'-SO_2X \qquad \text{III}$$

wherein R' is defined above, and X represents a halogen atom. The acyl group protecting the amino group, if present, can then be removed if desired.

The compounds of formula (II) include cadaverine (1,5-diaminopentane), 1,6-diaminohexane, 1,7-diaminoheptane, 1,8-diaminooctane and the like, or diaminoalkanes wherein one of the amino groups is protected by an acyl group such as acetyl, phthaloyl or carbobenzoxyl or a -CSSH group. The arylsulfonyl halides of formula (III) include p-toluenesulfonyl chloride, p-chlorobenzenesulfonyl chloride, p-bromobenzenesulfonyl chloride, α-naphthalenesulfonyl chloride, β-haphthalenesulfonyl chloride, 5-bromo-1-naphthalenesulfonyl chloride, 5-chloro-naphthalenesulfonyl chloride and the like.

When a compound of formula (II) is used in the present process, wherein the amino group is protected, the arylsulfonyl halide having the formula (III) is mixed with the aliphatic diamine, preferably in the presence of a solvent for the reaction. The molar ratio of the arylsulfonyl halide to the aliphatic diamine is preferably in the range of 0.5 – 5, especially 0.8 – 2. The ratio of the solvent to the arylsulfonyl halide is preferably in the range of 1 – 100. The reaction temperature can be in the range of −10° C to the boiling point of the solvent. If a dehydrohalogenating agent is used in the reaction, the amount of the aliphatic diamine can be advantageously decreased. Suitable solvents used in the reaction include water-acetone, water-ether, water-halohydrocarbon and the like. Suitable dehydrohalogenating agents include organic and inorganic alkaline compounds such as triethylamine, pyridine, caustic alkali, magnesia and the like. The compounds which are formed are sparingly soluble in water. Accordingly, substantially pure compounds can be obtained by sequentially washing the organic phase with a diluted alkaline solution, water, a diluted acid and water, in that order, and then removing the solvent, or by first removing the solvent and then washing the residue in the same manner. Thereafter, the protective group is removed by a conventional method to separate the product.

When a compound of formula (II) is used which does not have an amino protective group, i.e., the diaminoalkane, an arylsulfonyl halide of formula (III) is mixed with the diaminoalkane, preferably in the presence of a solvent for the reaction. The molar ratio of the arylsulfonyl halide to the aliphatic diamine is preferably in a range of 1 – 30, especially 2 – 10. The ratio of the solvent to the arylsulfonyl halide is preferably in the range of 2 – 200. The reaction temperature can be in a range of −10° C to the boiling point of the solvent used. Suitable solvents used include water, alkanols, water-acetone, dioxane and other solvents for diaminoalkanes. The residue obtained after removing the solvent is treated by the conventional method to separate the product.

The compounds of formula (I) in which R is an amino group are relatively difficult to dissolve in water (sparingly soluble). Accordingly, water-soluble impurities are removed by washing the impure product with water, and thereafter the product can be purified and separated as the hydrochloride salt thereof. However, when compound (I), wherein R is an acylated amino group is deacylated to yield the corresponding compound having a free amino group as R, for example, such as the decomposition of the phthalimide group by hydrazine hydrate, it is difficult to completely remove the by-product, 1,4-diketophthalazine in high efficiency by the above-mentioned operation. In this case, it is preferable to extract the product with a solvent such as chloroform, 1,2-dichloroethane or the like. The diaminoalkanes used in the invention are usually water-soluble. Therefore, an excess of diaminoalkane can be removed after the reaction by washing the residue from which the solvent is removed with water. The by-product, bis-acyl of the diaminoalkane is sparingly soluble in water or methanol, and therefore can be easily separated from the residue by removing excess diaminoalkane by washing the residue with water and then forming the hydrochloride salt thereof. The product is then removed with water or methanol.

When an unprotected diaminoalkane is used as the starting material, the yield is low compared to the case when a diaminoalkane with a protective group is used. However, the use of unprotected diaminoalkane is advantageous from the viewpoint of reaction operations and availability of the starting materials.

The ω-(arylsulfonamido)-alkylamines can also be produced by converting ω-(arylsulfonamido) alkanoic azides having the formula $$RSO_2NH(CH_2)_nCON_3$$

to the corresponding amines by the Curtius rearrangement reaction. The ω-(arylsulfonamido) alkanoic azides can be produced by reacting ω-(arylsulfonamido)-alkanoic acids or a functional derivative with hydrazine and nitrous acid or an alkali azide. The ω-(arylsulfonamido)-alkanoic acids in turn can be produced by reacting the corresponding aminoalkanoic acids with an arylsulfonyl halide. Suitable functional derivatives of the ω-(arylfulfonamido) alkanoic acids include anhydrides, esters or acid halides thereof. The esters and acid chlorides are preferably used. In the latter process, the ω-(arylsulfonamido) alkanoic acid or a functional derivative is mixed with hydrazine hydrate in a solvent for the reaction. Suitable solvents for this reaction include alkanols such as ethanol. The resulting acid hydrazide is mixed with nitrous acid and reacted to form the desired ω-(arylsulfonamido) alkanoic azide product. The reaction is usually conducted by mixing the hydrazide with a solution of sodium nitrite in the presence of a mineral acid such as hydrochloric acid.

The ω-(arylsulfonamido) alkanoic azides can also be produced by reacting a ω-(arylsulfonamido) alkanoic acid or a functional derivative thereof with thionyl chloride or phosphorus pentachloride and then reacting the resulting acid chloride with an alkali azide such as sodium azide. The ω-(arylsulfonamido) alkanoic azides are used in the Curtius rearrangement reaction without isolation because they easily decompose. The Curtius rearrangement reaction can be conducted under the usual rearrangement conditions. After the rearrangement, the product is hydrolyzed in the presence of an acid to yield the desired ω-(arylsulfonamido)-alkylamine. The product can be purified by any conventional method.

Studies have indicated that the compounds of formula (I) have a blood platelet aggregation inhibiting effect, and thus are effective preventive and therapeutic medicines for thrombosis in encephalo- and cardio-vascular systems. In order to study the blood platelet aggregation inhibiting effect of the compounds of the invention, a platelet rich plasma is prepared by centrifugal separation of a mixture of fresh human blood and 3.8% sodium citrate at a ratio of 9 : 1. The effects of the compounds on the blood platelet aggregation induced by collagen, adenosine diphosphate (ADP), epinephrine, thrombin, and the like are studied as shown in the Examples below.

Having generally described in invention, a further understanding can be obtained by reference to certain specific Examples which are provided herein for purposes of illustration only are not intended to be limiting unless otherwise specified.

Blood platelet aggregation was tested by the Aggregometer (manufactured by Bryston Co., Canada) in which the variation of light transmittance is measured. The light transmittance increases proportionally to the degree of aggregation of the blood platelets. The light transmittance of blood plasma from which blood platelets have been separated by centrifugal separation is rated as 100 and the light transmittance of a platelet rich plasma is rated as 0.

The light transmittance which increases by the aggregation is shown as the aggregation rate (%). The ralative aggregation rate (%) can be determined by dividing the aggregation rate by the aggregation rate of a control which has replaced the inhibitor compound by a buffered isotonic sodium chloride solution. The inhibition rate (%) for blood platelet aggregation by the compounds of the invention can be obtained by subtracting the relative aggregation rate from 100.

Collagen is prepared by dispersing 300 mg of insoluble collagen (manufactured by Sigma Co.) in 15 ml of an isotonic sodium chloride solution and then removing the rough particles by centrifugal sedimentation.

ADP is prepared by dissolving ADP in an isotonic sodium chloride solution in amounts of $3.7 \times 10^{-4}$ and maintaining the solution in a frozen condition. Immediately prior to use, the frozen solution was thawed and diluted to 8 times the volume with an isotonic sodium chloride solution.

Epinephrine is prepared by diluting a 1 mg/ml adrenaline solution (manufactured by Sankyo K.K.) to 20 times the volume with an isotonic sodium chloride solution.

Thrombin is prepared by dissolving 500 units of human-thrombin (manufactured by Midori Jyuji K.K.) in 2 ml of 50% glycerin and maintaining the same at $-20°$ C and diluting it to 20 times the volume with an isotonic sodium chloride solution.

The results of the blood platelet aggregation tests by collagen are shown in the following Table. The compounds (A) - (F) used in the tests are shown in the following examples.

Table 1

| Test condition | Test compound | Final concentration (M) | Aggregation rate (%) | Relative aggregation rate (%) | Inhibition rate (%) |
|---|---|---|---|---|---|
| Collagen 8μl number of blood platelets $35 \times 10^4$/c.mm | Control | | 92 | 100 | 0 |
| | Compound A | $4.4 \times 10^{-5}$ | 68 | 74 | 26 |
| | | $8.9 \times 10^{-5}$ | 0 | 0 | 100 |
| | Compound B | $4.4 \times 10^{-5}$ | 71 | 77 | 23 |
| | | $8.9 \times 10^{-5}$ | 0 | 0 | 100 |
| | Compound C | $8.9 \times 10^{-5}$ | 32 | 35 | 65 |
| | Compound D | $8.9 \times 10^{-5}$ | 28 | 30 | 70 |
| | Compound E | $7.4 \times 10^{-6}$ | 85 | 92 | 8 |
| | | $1.5 \times 10^{-5}$ | 8 | 9 | 91 |
| | | $4.4 \times 10^{-5}$ | 0 | 0 | 100 |
| | Compound F | $7.4 \times 10^{-6}$ | 92 | 100 | 0 |
| | | $1.5 \times 10^{-5}$ | 14 | 15 | 85 |
| | | $4.4 \times 10^{-5}$ | 0 | 0 | 100 |

Compound A  Example 1
Compound B  Example 2
Compound C  Example 3
Compound D  Example 4
Compound E  Example 6
Compound F  Example 7

As is clear from the results, compounds (E) and (F) are the most effective in inhibiting blood platelet aggregation. In the final concentration of $1.5 \times 10^{-5}$ M, the blood platelet aggregation by collagen was inhibited at a rate of about 80-100%. It was found that the inhibiting effect increases as a function of increasing contact time of the compound with the blood platelet, smaller numbers of blood platelets and smaller amounts of collagen. The compounds of the invention exhibit the same blood platelet aggregation inhibiting effect as in the aggregation of the platelets by epinephrine or thrombin. The compounds of the invention are not effective in the primary aggregation by ADP; however, they are substantially effective in the secondary aggregation by ADP. Accordingly, it is believed that the compounds of the invention inhibit irreversible aggregation caused by the discharge of various amines in the reaction and the coagulation promoter with morphologic variation of the blood platelets obtained by various stimulants. The effect of the compounds on blood vessels was examined by using isolated rabbit aorta in Rock's solution at 37° C. The isolated rabbit aorta were significantly relaxed in the presence of $1 \times - 10^{-4}$ M solutions of the compounds.

EXPERIMENT

The intravasation (injection of a substance into a blood vessel) of the compounds of the present invention on rabbits was conducted to study the effect of the compounds on blood platelet aggregation.

Effect of Compound B

The intravasation of 100 ml of a 2 mM solution of compound B (tris-buffered isotonic sodium chloride solution) on a rabbit (3.5 Kg weight) was gradually conducted. Before and after the intravasation, blood was sampled by a cardio-puncture in sequence. The blood platelet aggregation was studied by the above-described method and the results are shown in Table 2.

Table 2

|  | Aggregation rate by collagen (%) | Aggregation rate by adrenaline (%) |
|---|---|---|
| Before intravasation | 64.2 | 70.6 |
| After intravasation |  |  |
| 1 hour | 46 | 0 |
| 3 hours | 71 | 0 |
| 24 hours | 83 | 80.9 |

The intravasation of 12 ml of the 2 mM solution of compund B on a rabbit (3.3 Kg weight) was conducted. The results are shown in Table 3.

Table 3

|  | Aggregation rate by collagen (%) |
|---|---|
| Before intravasation | 69 |
| After intravasation |  |
| 2 hours | 0 |
| 4 hours | 60 |
| 24 hours | 68 |

2. EFFECT OF COMPOUND F

The intravasation of 6 ml of a 5 mM solution of compound F on a rabbit (4.3 Kg weight) was conducted. Before and after the intravasation, blood was sampled by a catheter inserted in the thigh artery. Blood platelet aggregation was studied by the above-mentioned method, and the results are shown in Table 4.

Table 4

|  | Aggregation rate by collagen (%) |
|---|---|
| Before intravasation | 64.4 |
| After intravasation |  |
| 30 min. | 54.4 |
| 1 hour | 46.6 |
| 2 hours | 37.6 |
| 4 hours | 0 |
| 5 hours | 0 |
| 6 hours | 25 |
| 24 hours | 70 |

PREPARATION OF 5-PHTHALIMIDOPENTYLAMINE HYDROCHLORIDE

A 32 g amount of ε-phthalimidecaproic acid was admixed with 80 ml of thionyl chloride and the mixture was kept at room temperature for about 1 hour until the generation of hydrogen chloride gas was finished. Thereafter, the solution was heated under reflux for 1 hour. After cooling, the product was condensed and dried. The residue was washed with n-hexane, and then was dissolved in 100 ml of acetone. The solution was added dropwise to a solution of 18 g of sodium azide in 50 ml of water at 10° C, in order to maintain the reaction temperature at 10°- 15° C. After addition of the solution, the upper phase of two phases of the reaction product, was separated. The upper phase liquid was added dropwise to 100 ml of benzene heated at 60° C, and the mixture was kept at 60° C for 2 hours until the generation of nitrogen gas was finished. The mixture was concentrated to about ⅓ the volume under reduced pressure, and 100 ml of 2N-HCl was added and the mixture was heated for 2 hours on a boiling water bath. The water phase was separated and concentrated and dried. The residue was recrystallized from ethanol, whereby 21.6 g of the following compound was obtained as colorless flaky crystals having a melting point of 211°- 213° C (yield 66%).

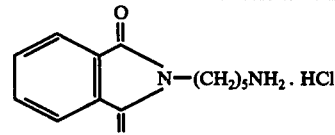

| Elemental analysis: | $C_{13}H_{17}N_2O_2Cl$ | | |
|---|---|---|---|
|  | C | H | N |
| Calculated: | 58.09 | 6.38 | 10.43 |
| Found: | 58.62 | 6.44 | 10.45 |

PREPARATION OF 6-ACETAMIDOHEXYLAMINE

A 50.1 g amount of 1,6-diaminohexane was admixed with 20 ml of water and 13.2 g of ethyl acetate to form a solution. The solution was kept at room temperature for 2 days and then water and ethanol were removed by distillation. The residue was distilled under reduced pressure. When 30 g of 1,6-diaminohexane were distilled as a fraction having a boiling point of 82°- 84° C (12 mmHg), 14.9 g of 6-acetamidohexylamine were obtained as a fraction having a boiling point of 170°- 175° C (7 mmHg) (yield 65.8%).

The hydrochloride product was colorless needle-like crystals having a melting point of 142°- 143° C (recrystallized from ethanol)

| Elemental analysis: | $C_8H_{19}N_2OCl$ | | |
|---|---|---|---|
|  | C | H | N |
| Calculated: | 49.35 | 9.84 | 14.39 |

-continued

| Elemental analysis: | C₈H₁₉N₂OCl | | |
|---|---|---|---|
| | C | H | N |
| Found: | 49.18 | 10.05 | 14.38 |

EXAMPLE 1

A 4.8 g amount of 5-phthalimidopentylamine hydrochloride was suspended in a solution of 3.3 g of sodium bicarbonate in 20 ml of water, and the mixture was stirred at room temperature for 5 minutes, and then 50 ml of chloroform were added. A 100 ml amount of the chloroform solution of 5 g of 5-bromo-1-naphthalenesulfonyl chloride was added to the solution with stirring to react the components at room temperature for 1.5 hours. The chloroform phase was separated and washed sequentially with an aqueous solution of sodium bicarbonate, water, diluted hydrochloric acid and water and was dried with sodium sulfate. Thereafter, chloroform was removed by distillation. The residue was recrystallized sequentially from chloroform-ethanol and 200 times the amount of ethanol whereby 7.9 g of the following compound as yellow prismatic crystals having a melting point of 157°– 158° C (yield 96%) were obtained.

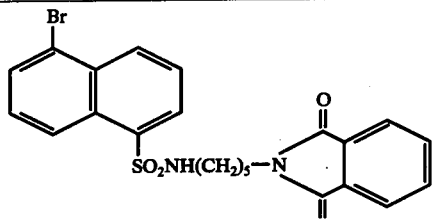

| Elemental analysis: | C₂₃H₂₁O₄N₂SBr | | |
|---|---|---|---|
| | C | J | M |
| Calculated: | 55.09 | 4.22 | 5.59 |
| Found: | 55.19 | 4.04 | 5.61 |

A 5 g amount of the resulting N-(5'-phthalimidopentyl)-5-bromo-1-naphthalene-sulfonamide was added to 50 ml of ethanol and the compound was dissolved by heating on a hot water bath for about 20 minutes. A 1 ml amount of 100% hydrazine hydrate was added to the solution, the mixture was heated under reflux for 1.5 hours, and then it was condensed and dried. A 15 ml amount of 2N-HCl was added to the residue and the mixture was heated on a boiling water bath for 30 minutes. The isoluble material was filtered and was washed with hot water. The mother liquor and the wash liquid were mixed and a concentrated ammonia solution was added until the solution became alkaline. The solution was extracted with chloroform and the chloroform solution was dried with sodium sulfate. Chloroform was removed by distillation and the residue was admixed with 0.7 ml of 2N-HCl and heated to dissolve the residue. The solution was concentrated and dried. The residue was recrystallized from ethanol whereby 3.5 g of the following compound as colorless plate crystals having a melting point 216° – 217° C (yield 80%) were obtained.

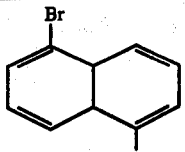
SO₂NH(CH₂)₅NH₂ . HCl

| Elemental analysis: | C₁₅H₂₀N₂O₂SBrCl | | |
|---|---|---|---|
| | C | H | N |
| Calculated: | 44.18 | 4.94 | 6.87 |
| Found: | 44.09 | 4.79 | 6.85 |

EXAMPLE 2

A 13.5 g amount of 5-phthalimidopentylamine hydrochloride was added to 71 ml of an aqueous solution of 8.1 g of sodium bicarbonate with stirring to form a solution. A 71 ml amount of acetone, and 130 ml of an acetone solution of 11.8 g of 5-chloro-1-naphthenesulfonyl chloride were sequentially added to the solution with stirring, and the components were reacted at room temperature for 1 hour. The mixture was heated to 50° C and was cooled to room temperature with stirring. The reaction mixture was placed into about 500 ml of water. The insoluble materials were filtered and were sequentially washed with 0.2N-HCl and water and then air dried. Thereafter, the materials were recrystallized from ethanol whereby 19.6 g of the following compound as colorless prismatic crystals having a melting point of 143°–145° C (yield 95.6%) were obtained.

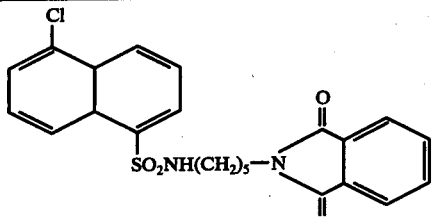

| Elemental analysis: | C₂₃H₂₁O₄N₂SCl | | |
|---|---|---|---|
| | C | H | N |
| Calculated: | 60.45 | 4.63 | 6.13 |
| Found: | 60.52 | 4.44 | 6.03 |

A 18.5 g amount of the resulting N-(5'-phthalimidopentyl)-5-chloro-1-naphthalenesulfonamide was dissolved in 185 ml of hot ethanol. A 6.1 g amount of 100% hydrazine hydrate was added to the mixture which was heated under reflux for 2 hours. After cooling the solution, the precipitate was filtered and washed with ethanol, and then dissolved in chloroform. The chloroform solution was sequentially washed with 5% NaOH and water and then dried with sodium sulfate. Thereafter, chloroform was removed by distillation. The residue was dissolved in methanol and concentrated hydrochloric acid was added to adjust the pH of the solution to 2 and the solvent was removed by distillation. The product was recrystallized from ethanol whereby 11.2 g of the following compound as colorless flaky crystals having a melting point of 210° – 211° C (yield 76.2%) were obtained.

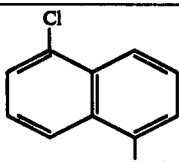

SO₂NH(CH₂)₅NH₂ . HCl

| Elemental analysis: | C₁₅H₂₀N₂O₂SCl₂ | | |
|---|---|---|---|
| | C | H | N |
| Calculated: | 45.59 | 5.55 | 7.71 |
| Found: | 49.76 | 5.54 | 7.67 |

EXAMPLE 3

A 20 ml amount of ethyl ether was added to 24 ml of an aqueous solution of 4.74 g of 6-acetamidohexylamine. A 6.8 g amount of α-naphthalenesulfonyl chloride and 4 ml of 7.5 N-NaOH were added alternately little by little to the mixture with stirring. The mixture was stirred at room temperature for 3 hours. The reaction product was extracted with chloroform and the chloroform solution was washed with water and dried with sodium sulfate. Thereafter, the chloroform was removed by distillation and an oily residue was obtained. The oily residue was dissolved in 50 ml of ethanol and was added to 120 ml of a 10% aqueous solution of sodium hydroxide. The mixture was heated under reflux for 8 hours. After cooling the solution, concentrated hydrochloric acid was added to adjust the pH to 1 and the mixture was concentrated and dried under a reduced pressure. The residue was admixed with methanol and the insoluble inorganic materials were separated. Methanol was then removed by distillation and the product was recrystallized from ethanol whereby 5.7 g of the following compound as colorless needle-like crystals having a melting point of 158° - 160° C (yield 55.5%) were obtained.

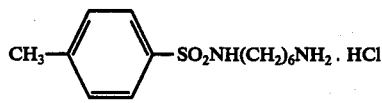

SO₂NH(CH₂)₆NH₂ . HCl

| Elemental analysis: | C₁₆H₂₃O₂N₂SCl | | |
|---|---|---|---|
| | C | H | N |
| Calculated: | 56.05 | 6.76 | 8.17 |
| Found: | 56.15 | 6.69 | 8.15 |

EXAMPLE 4

The process of Example 3 was repeated except that 6.8 g of β-naphthalenesulfonyl chloride were used instead of α-naphthalenesulfonyl chloride. A 5.2 g amount of the following compound as colorless needle-like crystals having a melting point of 156° - 157° C (yield 51%) was obtained.

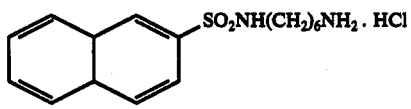

SO₂NH(CH₂)₆NH₂ . HCl

| Elemental analysis: | C₁₆H₂₃N₂O₂SCl | | |
|---|---|---|---|
| | C | H | N |
| Calculated: | 56.05 | 6.76 | 8.17 |
| Found: | 56.08 | 6.79 | 8.23 |

EXAMPLE 5

The process of Example 3 was repeated except that 5.7 g of p-toluenesulfonyl chloride was used instead of α-naphthalenesulfonyl chloride and the product was recrystallized from ethanol-ethyl ether whereby 5.1 g of the following compound as colorless needle-like crystals having a melting point of 96° - 97° C (yield 55.5%) were obtained.

CH₃—⌬—SO₂NH(CH₂)₆NH₂ . HCl

| Elemental analysis: | C₁₃H₂₃N₂O₂SCl | | |
|---|---|---|---|
| | C | H | N |
| Calculated: | 50.88 | 7.56 | 9.13 |
| Found: | 51.02 | 7.46 | 9.42 |

EXAMPLE 6

A 6.97 g amount of 1,6-diaminohexane was dissolved in 80 ml of dioxane and 3.05 g of 5-bromo-1-naphthalenesulfonyl chloride powder was added to the solution with vigorous stirring at room temperature to form a slurry. The slurry was stirred for 1 hour, was heated for 30 minutes on a boiling water bath and was dried under reduced pressure. The residue was admixed with water and the insoluble materials were filtered and dried in air. The product was admixed with 200 ml of methanol; the mixture was heated; and the insoluble bis-acyl compound was filtered. Concentrated hydrochloric acid was added to the mother liquor to adjust the pH to 2 and the solvent was removed by distillation. The residue was recrystallized from ethanol whereby 1.98 g of the following compound as colorless plate-like crystals having a melting point of 228°–229° C (yield 47%) were obtained.

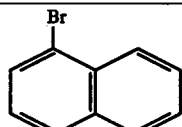

SO₂NH(CH₂)₆NH₂ . HCl

| Elemental analysis: | C₁₆H₂₂N₂O₂SClBr | | |
|---|---|---|---|
| | C | H | N |
| Calculated: | 45.56 | 5.26 | 6.64 |
| Found: | 45.56 | 5.22 | 6.68 |

EXAMPLE 7

The process of Example 6 was repeated except that 2.61 g of 5-chloro-1-naphthalenesulfonyl chloride was used instead of 5-bromo-1-naphthalenesulfonyl chloride whereby 2.3 g of the following compound as colorless needle-like crystals having a melting point of 219° C (yield 61%) were obtained.

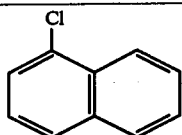

SO₂NH(CH₂)₆NH₂ . HCl

Elemental analysis: C₁₆H₂₂N₂O₂Cl₂

|  | C | H | N |
|---|---|---|---|
| Calculated: | 50.92 | 5.88 | 7.43 |
| Found: | 51.02 | 5.83 | 7.43 |

EXAMPLE 8

A 2 g amount of 1,7-diaminoheptane was dissolved in 70 ml of dioxane and 0.8 g of 5-bromo-1-naphthalenesulfonyl chloride was added to the solution with vigorous stirring. The mixture was stirred at room temperature for 1 hour and was heated for 30 minutes on a boiling water bath to react the components. The solvent was removed by distillation and water was added to the residue. The insoluble material was filtered and washed with water, and dissolved in methanol. The insoluble bisacyl compound was removed by filtration. Concentrated hydrochloric acid was added to the mother liquor to adjust the pH to 2 and the solution was concentrated and dried. The residue was washed with water, dried, and recrystallized from ethanol whereby 0.8 g of the following compound as colorless plate-like crystals having a melting point of 208° – 210° C (yield 70.2%) were obtained.

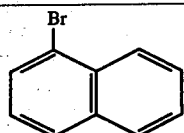

SO₂NH(CH₂)₇NH₂ . HCl

Elemental analysis: C₁₇H₂₄N₂O₂SBrCl

|  | C | H | N |
|---|---|---|---|
| Calculated: | 46.85 | 5.55 | 6.43 |
| Found: | 46.75 | 5.51 | 6.39 |

EXAMPLE 9

A 3.7 g amount of 1,8-diamino-octane was dissolved in 100 ml of dioxane and 1.55 g of 5-bromo-1-naphthalenesulfonyl chloride powder was added to the solution with vigorous stirring at room temperature to form a slurry. The slurry was stirred for 1 hour and heated for 30 minutes on a boiling water bath. The slurry was then concentrated and dried. The residue was admixed with water and the insoluble material was filtered, washed with water and dried in air. The product was admixed with 200 ml of methanol and the mixture was heated under reflux for 30 minutes. The insoluble bis-acyl compound was filtered hot. The mother liquor was treated with activated carbon and 2N-HCl was added to the solution to adjust the pH to 2. The mixture was concentrated and dried. The residue was recrystallized from ethanol whereby 1.5 g of the following compound as colorless plate-like crystals having a melting point of 216° – 217° C (yield 66%) were obtained.

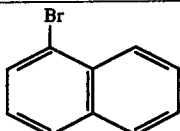

SO₂NH(CH₂)₈NH₂ . HCl

Elemental analysis: C₁₈H₂₆O₂N₂BrCl

|  | C | H | N |
|---|---|---|---|
| Calculated: | 48.06 | 5.83 | 6.23 |
| Found: | 48.09 | 5.86 | 6.21 |

EXAMPLE 10

A 6.64 g amount of 1,8-diamino-octane was dissolved in 120 ml of dioxane, and 2.11 g of p-chlorobenzenesulfonyl chloride was added to the solution with vigorous stirring at room temperature to form a slurry. The mixture was stirred for 1 hour, heated on a boiling water bath for 30 minutes, concentrated and dried. The residue was admixed with water and the insoluble material was filtered and washed with water. The product was suspended in water and concentrated hydrochloric acid was added to the suspension to adjust the pH to 2. The mixture was heated in a boiling water bath and the insoluble bis-acyl compound was filtered hot. The mother liquor was concentrated and dried. The resulting residue was recrystallized about 5 times from water and further recrystallized from ethanol-isopropyl ether whereby 1.6 g of the following compound as colorless plate-like crystals having a melting point of 188° – 200° C (yield 45%) were obtained.

Elemental analysis: C₁₄H₂₄O₂N₂SCl₂

|  | C | H | N |
|---|---|---|---|
| Calculated: | 47.32 | 6.81 | 7.85 |
| Found: | 47.40 | 6.81 | 7.84 |

EXAMPLE 11

ε-(p-Chlorobenzenesulfonamido) caproic acid ethyl ester was produced by reacting ε-aminocaproic acid with p-chlorobenzenesulfonyl chloride and then reacting the product with ethanol in the presence of conc. sulfuric acid. A mixture of 15.0 g of ε-(p-chlorobenzenesulfonamido) caproic acid ethyl ester, 9 ml of ethanol and 18 ml of 100% hydrazine hydrate was heated under reflux for 1.5 hours. The reaction mixture was condensed, dried and the residue was recrystallized from ethanol whereby 13.5 g of ε-(p-chlorobenzenesulfonamido) caproic acid hydrazide as colorless needle-like crystals having a melting point of 128° – 129° C (yield 94.0%) were obtained.

A 3.02 g of the intermediate was admixed with 25 ml of 2 N HCl to produce the hydrochloride thereof. A solution of 0.83 g of sodium nitrite in 3 ml of water was added dropwise to the solution at 5° – 10° C with stirring and the reaction was conducted at 50° – 60° C for 1 hour. After cooling the reaction mixture to room temperature, the impurities were extracted with dichloroethane. Ammonia water was added to the extracted solution until alkaline. The product was extracted with dichloroethane, the extract was dried and the solvent removed by distillation. The residue was recrystallized from dichloroethane whereby 1.86 g of 5-(p-chlorobenzenesulfonamido)-n-pentylamine as colorless needle-like crystals having a melting point of 102.5° – 105.0° C were obtained.

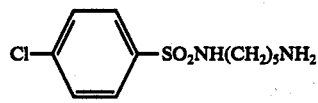

EXAMPLE 12

The process of Example 11 was repeated except that 15.0 g of ε-(benzenesulfonamido)-caproic acid ethyl ester was used and the product was recrystallized from ethanol-ether whereby 10.5 g of ε-(benzenesulfonamido) caproic acid hydrazide as colorless needle-like crystals having a melting point of 81° – 83° C (yield 73.5%) were obtained. Thereafter, 2.85 g of the intermediate were treated whereby 1.22 g of 5-(benzenesulfonamido)-n-pentylamine as colorless prismatic crystals having a melting point of 76°–77°C (yield 50.4%) were obtained.

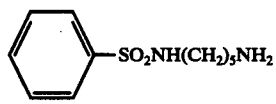

EXAMPLE 13

The process of Example 11 was repeated except that 15.0 g of ε-(p-toluenesulfonamido) caproic acid ethyl ester were used and the product of the reaction was recrystallized from ethanol-ether whereby 11.5 g of ε-(p-toluenesulfonamido) caproic acid hydrazide as colorless needle-like crystals (yield 80.3%) were obtained as an intermediate. A 2.99 g amount of ε-(p-toluenesulfonamido) caproic acid hydrazide was admixed with 25 ml of 2N-HCl to form the hydrochloride and 20 ml of ether was added to the solution. A solution of 0.83 g of sodium nitrite in 3 ml of water was added dropwise to the mixture at 10° – 15° C with stirring and the reaction was conducted for 5 – 10 minutes. The ether phase of the reaction product was separated, washed with water, and the solvent was removed by distillation. The resulting oily azide was admixed with 20 ml of 2N-HCl at 50°–60° C with vigorous stirring for 3 hours. The reaction product was concentrated and dried under reduced pressure. The residue was admixed with acetone, and the insoluble material was filtered and washed with acetone and recrystallized from methanol-ether whereby 2.02 g of 5-(p-toluenesulfonamido)-n-pentylamine hydrochloride as pale yellow needle-like crystals having a melting point of 122° – 123° C (yield 69.2%) were obtained.

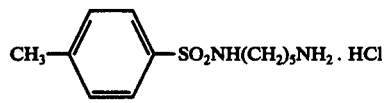

EXAMPLE 14

A mixture of 9.5 g of ε-(α-naphthalenesulfonamide)-caproic acid ethyl ester, 6 ml of ethanol and 10 ml of 100% hydrazine hydrate was heated under reflux for 1.5 hours. The reaction mixture was concentrated and 50 ml of 2N-HCl was admixed with the residue whereby 8.9 g of ε-(α-naphthalenesulfonamido) caproic acid hydrazide hydrochloride as pale yellow flake-like crystals having a melting point of 163° – 165° C (yield 88.3%) were obtained. The process of Example 13 was repeated using 3.72 g of ε- (α-naphthalenesulfonamido) caproic acid hydrazide hydrochloride, whereby 2.37 g of 5- (α-naphthalenesulfonamido)-n-pentylamine hydrochloride as pale yellow flake-like crystals having a melting point of 211° – 213° C (yield 72.5%) were obtained.

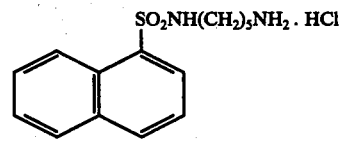

EXAMPLE 15

A mixture of 8.0 g of ε-(β-naphthalenesulfonamido) caproic acid ethyl ester, 5 ml of ethanol and 9 ml of 100% hydrazine hydrate was heated under reflux for 1.5 hours, and the reaction product was treated in accordance with the process of Example 11 whereby 6.9 g of ε-(β-naphthalenesulfonamido) caproic acid hydrazide as colorless flake-like crystals having a melting point of 106° – 107° C (yield 89.8%) were obtained. The process of Example 13 was repeated except that 3.35 g of ε-(β-naphthalenesulfonamido) caproic acid hydrazide was used whereby 1.97 g of 5-(β-naphthalenesulfonamido)-n-pentylamine hydrochloride as colorless flake-like crystals having a melting point of 163°–164° C (yield 60.2%) were obtained.

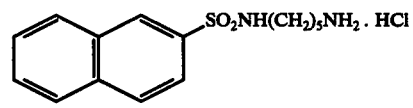

EXAMPLE 16

A 3.20 g amount of ε-(p-chlorobenzenesulfonamido) caproic acid hydrazide was admixed with 25 ml of 2N-HCl to form the hydrochloride, and then 20 ml of ether was added. A solution of 0.83 g of sodium nitrite in 3 ml of water was added dropwise to the solution at 10° –15° C with stirring. The reaction was conducted for 5 minutes. The insoluble material was filtered. The ether phase of the filtrate was separated and washed with water and the solvent was removed by distillation at a temperature base lower than 20° C. The resulting azide was admixed with 20 ml of 2N HCl and the mixture was vigorously stirred for 3 hours. The reaction mixture was concentrated and dried under reduced pressure. The residue was admixed with acetone and the precipitate was filtered and washed with acetone and recrystallized from methanol-ether whereby 1.82 g of 5-(p-chlorobenzenesulfonamido)-n-pentylamine hydrochloride as colorless prismatic crystals having a melting point of 156° – 157° C (yield 60.1%) were obtained.

EXAMPLE 17

A mixture of 5.4 g of ε-(benzenesulfonamido) caproic acid, 50 ml of benzene and 2.8 g of thionyl chloride was heated under reflux for 50 minutes, and then was concentrated. The resulting oily acid chloride was dissolved in 20 ml of ether. A solution of 1.9 g of sodium azide in 20 ml of water was added to the solution as it was cooled with ice. The reaction was conducted for 45 minutes with vigorous stirring. The ether phase of the reaction mixture was separated and washed sequentially with a 5% aqueous solution of sodium bicarbonate and water. The solvent was removed by distillation at a temperature less than 20° C. The resulting azide was admixed with 50 ml of 2N HCl at 50° – 60° C for 3 hours with vigorous stirring. The product was cooled with water and the by-product was extracted with ethyl acetate. The residual water phase was concentrated and the residue was admixed with acetone. The precipitate obtained was filtered after cooling with ice and was recrystallized from methanol-ether whereby 2.3 g of 5-(benzenesulfonamido)-n-pentylamine hydrochloride as colorless prismatic crystals having a melting point of 130° – 131° C (yield 41.5%) were obtained.

Having now fully described this invention, it will be apparent to one of ordinary skill in the art that many changes and modifications can be made thereto without departing from the spirit or scope of the invention as set forth herein.

What is claimed as new and intended to be covered by letters patent is:

1. A ω-(arylsulfonamido)alkylamine having the formula

wherein R' is halonaphthyl; and $n$ is an integer of 5 – 8.

2. The compound of claim 1 wherein R' is 5-halo-1-naphthyl.

3. The compound of claim 1 wherein R' is 5-halo-2-naphthyl.

4. The compound of claim 2 wherein halo is Br and $n$ is 6.

5. The compound of claim 2 wherein halo is Cl and $n$ is 6.

6. The compound of claim 2 wherein halo is Br and $n$ is 5.

7. The compound of claim 2 wherein halo is Cl and $n$ is 5.

8. The compound of claim 3 wherein halo is Br and $n$ is 6.

9. The compound of claim 3 wherein halo is Cl and $n$ is 6.

* * * * *